(12) United States Patent
Misaki et al.

(10) Patent No.: US 8,920,840 B2
(45) Date of Patent: Dec. 30, 2014

(54) ENTERIC TABLET

(75) Inventors: Masafumi Misaki, Osaka (JP); Yuki Tsushima, Osaka (JP); Masahiro Niwa, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 13/695,220

(22) PCT Filed: Apr. 28, 2011

(86) PCT No.: PCT/JP2011/060478
§ 371 (c)(1),
(2), (4) Date: Jan. 7, 2013

(87) PCT Pub. No.: WO2011/136373
PCT Pub. Date: Nov. 3, 2011

(65) Prior Publication Data
US 2013/0115291 A1    May 9, 2013

(30) Foreign Application Priority Data
Apr. 30, 2010    (JP) ................. 2010-105668

(51) Int. Cl.
A61K 9/28     (2006.01)
A61K 31/451   (2006.01)
A61K 31/4465  (2006.01)
A61K 9/20     (2006.01)

(52) U.S. Cl.
CPC ............ *A61K 9/2077* (2013.01); *A61K 9/2846* (2013.01); *A61K 31/4465* (2013.01); *A61K 9/2813* (2013.01); *A61K 9/2886* (2013.01)
USPC ............ 424/480; 424/482; 424/479; 514/317

(58) Field of Classification Search
None
See application file for complete search history.

(56) References Cited

U.S. PATENT DOCUMENTS

| 7,732,463 B2 * | 6/2010 | Puschl et al. .................. 514/317 |
| 2003/0147950 A1 | 8/2003 | Platteeuw et al. |
| 2003/0147955 A1 | 8/2003 | Platteeuw et al. |
| 2003/0180352 A1 * | 9/2003 | Patel et al. .................... 424/465 |
| 2006/0134216 A1 | 6/2006 | Farrell et al. |
| 2007/0060574 A1 | 3/2007 | Ruhland et al. |
| 2007/0190129 A1 * | 8/2007 | Ahmed et al. ................ 424/451 |
| 2009/0318482 A1 * | 12/2009 | Ono et al. ..................... 514/274 |
| 2010/0137366 A1 | 6/2010 | Miller |
| 2010/0144788 A1 | 6/2010 | Stensbol et al. |
| 2011/0053978 A1 | 3/2011 | Miller et al. |
| 2012/0189697 A1 | 7/2012 | Hojer et al. |

FOREIGN PATENT DOCUMENTS

| EP | 1 441 713 | 8/2007 |
| JP | 2008-524257 | 7/2008 |
| WO | 03/029232 | 4/2003 |
| WO | 2007/144006 | 12/2007 |
| WO | WO-2007-144006 | * 12/2007 |
| WO | 2008/113360 | 9/2008 |
| WO | 2009/060952 | 5/2009 |
| WO | 2009/076962 | 6/2009 |
| WO | 2011/023194 | 3/2011 |

* cited by examiner

*Primary Examiner* — Frederick Krass
*Assistant Examiner* — Celeste A Roney
(74) *Attorney, Agent, or Firm* — Hamre, Schumann, Mueller & Larson, P.C.

(57) ABSTRACT

The present invention relates to an enteric tablet with improved bioavailability, which is rapidly disintegrated after reaching the intestine to allow dissolution of the active ingredient, and which characteristically reduces the amount of talc to be used and is free of an alkali component.

3 Claims, No Drawings

ENTERIC TABLET

TECHNICAL FIELD

The present invention relates to an enteric tablet superior in acid resistance, which does not permit dissolution of a medicament during residence in the stomach and immediately after excretion from the stomach, and permits dissolution of the medicament for the first time after reaching the intestine.

BACKGROUND ART

Enteric coating has been widely used for various purposes of mainly protecting medicaments unstable to acid from the gastric acid, protecting gastric mucous membrane from medicaments stimulating or damaging the stomach wall, and the like. Many tablets containing an active ingredient and an alkali component, which are coated with an enteric coating agent are known (patent documents 1-17). In addition, use of a methacrylic acid copolymer as an enteric coating agent is known. The methacrylic acid copolymer is commercially available as EUDRAGIT (registered trade mark); manufactured by Evonik Industries AG) polymer. In addition, Acryl-EZE (manufactured by Colorcon Ltd.) added with sodium bicarbonate (alkali component) as an enteric coating substrate in advance for improving polymer dispersibility is also commercially available. Moreover, it is known that talc is generally used as a lubricant in an enteric coating agent, and the content of talc is preferably 50% (weight ratio) relative to the polymer component (non-patent document 1).

As a compound showing a serotonin reuptake inhibitory action, and useful for treating affective disorders, such as depression, and anxiety disorders including generalized anxiety disorder, panic disorder and obsessive disorder, 4-[2-(phenylsulfanyl)phenyl]piperidine derivatives (patent documents 18, 19) are known.

PRIOR ART

Patent Documents

[patent document 1] U.S. Pat. No. 4,539,198
[patent document 2] U.S. Pat. No. 5,711,967
[patent document 3] WO98/27967
[patent document 4] WO2001/058424
[patent document 5] US-A-2005/025824
[patent document 6] US-A-2004/028737
[patent document 7] WO2004/108067
[patent document 8] WO2004/096208
[patent document 9] WO2005/041934
[patent document 10] US-A-2005/118256
[patent document 11] WO2005/055955
[patent document 12] WO2005/072709
[patent document 13] WO2005/077420
[patent document 14] WO2005/099666
[patent document 15] WO2005/105036
[patent document 16] WO2005/105045
[patent document 17] WO2006/014973
[patent document 18] WO2003/029232
[patent document 19] WO2008/113358

Non-Patent Document

[non-patent document 1] Guideline for Formulation Development and Process Technology for Enteric Coatings, EVONIK INDUSTRIES, Pharma Polymers March 2009, 3.1e

DISCLOSURE OF THE INVENTION

Problems to be Solved by the Invention

It is an object of the present invention to improve, in an oral tablet containing 4-[2-(4-dimethylphenylsulfanyl)phenyl]piperidine or a salt thereof as an active ingredient, acid resistance of the preparation and bioavailability of the active ingredient.

Means of Solving the Problems

The present inventors have conducted intensive studies in an attempt to solve the aforementioned problems and found that dissolution of the active ingredient during residence in the stomach and immediately after excretion from the stomach can be suppressed by forming an enteric coating layer containing talc in a weight of 40% or less of the polymer component and substantially free of an alkali component, as a result of which the bioavailability and acid resistance of the active ingredient can be improved, which resulted in the completion of the present invention.

Accordingly, the present invention relates to
[1] an enteric tablet comprising 1) a core tablet comprising 4-[2-(4-methylphenylsulfanyl)phenyl]piperidine or a salt thereof,
2) an enteric coating layer comprising a) one or more kinds of polymer components selected from methacrylic acid copolymer, hypromellose phthalate, hypromellose acetate succinate, cellulose acetate phthalate and polyvinyl acetate phthalate, and
b) talc in a weight of 40% or less of said polymer component(s), and c) substantially no alkali component,
[2] the enteric tablet of the above-mentioned [1], wherein the polymer component is a methacrylic acid copolymer comprised of 1) methacrylic acid, and
2) one or more kinds of monomers selected from methyl acrylate, ethyl acrylate and methyl methacrylate,
[3] the enteric tablet of the above-mentioned [2], wherein the methacrylic acid copolymer is
1) a copolymer of methacrylic acid and ethyl acrylate,
2) a copolymer of methacrylic acid and methyl methacrylate, or
3) a copolymer of methacrylic acid, methyl acrylate and methyl methacrylate,
[4] the enteric tablet of the above-mentioned [1], wherein the content of the talc is 10 to 25 wt % of the polymer component,
[5] the enteric tablet of the above-mentioned [1], wherein the talc has an average particle size (volume average particle size: median diameter D50) of 0.1 μm-15 μm,
[6] the enteric tablet of the above-mentioned [1], wherein the enteric coating layer further comprises a plasticizer,
[7] the enteric tablet of the above-mentioned [1] wherein the weight of the polymer component to the surface area of the core tablet is 4 to 6 mg/cm$^2$.

Effect of the Invention

Using the enteric tablet of the present invention, infiltration of the gastric juice into a tablet can be prevented by improved acid resistance of the tablet, which in turn suppresses gelation of the tablet and permits rapid disintegration after reaching the intestine and dissolution of the active ingredient. As a result, the bioavailability of the active ingredient is improved. The enteric tablet of the present invention is safe and non-toxic, and can be effectively administered to human.

DETAILED DESCRIPTION OF THE INVENTION

The present invention is explained in detail in the following.

In the present specification, the "enteric tablet" means a tablet having a core containing an active ingredient, which is coated with an enteric coating substrate containing an enteric polymer. The present invention preferably provides an enteric tablet wherein a core containing an active ingredient is coated with an enteric coating substrate containing an enteric polymer. Hereinafter the enteric tablet of the present invention is sometimes to be also referred to as the tablet of the present invention.

In the present specification, the layer constituted with an enteric coating substrate in the enteric tablet is to be referred to as an enteric coating layer.

The core containing an active ingredient is not particularly limited regarding its form as long as it can be later coated with an enteric coating substrate, and tablets, fine granules, granules, tablets obtained by compression molding fine granules or granules and the like can be mentioned. For production of an enteric tablet, a tablet form is preferable. In the following, a core containing an active ingredient, which is in the form of a tablet, is also referred to as a core tablet.

In the present specification, the "enteric coating substrate" means a substance containing an enteric polymer, a lubricant, a plasticizer, a pigment and the like, and means a substrate for coating the aforementioned core containing an active ingredient.

In the present specification, the "enteric polymer" is not particularly limited and, for example, one or more kinds of polymer components selected from methacrylic acid copolymer, hydroxypropylmethylcellulose phthalate (hereinafter to be also referred to as hypromellose phthalate), hydroxypropylmethylcellulose acetate succinate (hereinafter to be also referred to as hypromellose acetate succinate), cellulose acetate phthalate, polyvinyl acetate phthalate, carboxymethylethylcellulose, shellac and the like can be mentioned. Among these, one or more kinds of polymer components selected from methacrylic acid copolymer, hypromellose phthalate, hypromellose acetate succinate, cellulose acetate phthalate and polyvinyl acetate phthalate are preferable. Particularly, a methacrylic acid copolymer is preferable, a methacrylic acid copolymer constituted with 1) methacrylic acid, and 2) one or more kinds of monomers selected from methylacrylate, ethylacrylate and methylmethacrylate is more preferable, and 1) a copolymer of methacrylic acid and ethylacrylate, 2) a copolymer of methacrylic acid and methylmethacrylate, or 3) a copolymer of methacrylic acid, methylacrylate and methylmethacrylate is particularly preferable.

While the amount of the enteric polymer to be applied varies depending on the size, form and the like of the core containing the active ingredient, when the core is a tablet, it is generally about 4 to 8 $mg/cm^2$, preferably about 4 to 6 $mg/cm^2$, based on the surface area of the core, from the aspects of acid resistance and disintegration property.

In the tablet of the present invention, the enteric coating layer characteristically contains at least talc as a lubricant. Talc is contained in a weight of 40% or less relative to the above-mentioned polymer components. In the present specification, unless otherwise specified, the weight ratio to the polymer components means the weight ratio to the weight of the dry polymer components. Talc to be used is preferably of a fine particle grade, specifically, one having an average particle size (volume average particle size; median size D50) of 0.1 μm-15 μm, preferably 1 μm-10 μm When the weight exceeds 40%, talc is not uniformly dispersed, thus causing problems in the productivity of the tablet. In addition, talc is preferably contained in about 10% to allow it to function as a lubricant. From the aspect of dispersibility, talc is preferably contained at a weight ratio of 10-25% relative to the above-mentioned polymer components. Such amount of the talc to be used is significantly smaller than the amount generally used or recommended in this field.

In the enteric coating layer, since talc is dispersed as an insoluble component, a smaller amount and a smaller particle size decrease water permeability of the membrane, whereby improvement of acid resistance can be expected. Furthermore, since talc is in a dispersion state during preparation of the enteric coating substrate, the dispersion state of small amount and small particle size of talc is improved, which prevents sedimentation of the talc during the coating step and enables formation of a uniform membrane of the enteric coating layer.

Moreover, in addition to talc, other lubricant can be contained. Examples of such lubricant include magnesium stearate, sucrose ester of fatty acid, polyethylene glycol, stearic acid and the like.

In the tablet of the present invention, the enteric coating layer can contain a plasticizer as necessary. In the present specification, while the "plasticizer" is not particularly limited, triethyl citrate, acetyltributyl citrate, glycerol acetic acid fatty acid ester, triacetine, dibutylphthalate, polysorbate 80, polyethylene glycol, propylene glycol, a mixture thereof, and the like can be mentioned, with preference given to triethyl citrate. From the aspect of membrane formability of the enteric coating layer, the plasticizer is generally contained in a weight ratio of 5 to 70% relative to the above-mentioned polymer components, and those of ordinary skill in the art can determine the content depending on the kind of the polymer. When a methacrylic acid copolymer (dispersion) is used, it is preferably contained in a weight ratio of about 10 to 20%.

In the tablet of the present invention, the enteric coating layer can contain a pigment as necessary. In the present specification, the "pigment" is used to mean colorant, coloring agent, dye and the like and, for example, titanium dioxide, iron oxide (red, yellow), Food Color Yellow No. 5, Food Color Blue No. 2 and the like can be mentioned.

In the tablet of the present invention, the enteric coating layer is characteristically substantially free of an alkali component. Here, the alkali component means, for example, components such as sodium bicarbonate, sodium hydroxide, sodium carbonate, magnesium carbonate and the like added to Acryl-EZE manufactured by Colorcon Ltd. for the purpose of improving dispersibility of the polymer.

Here, being "substantially free of an alkali component" means that an alkali component is not added, where the presence or absence of a trace amount of an alkali component, which does not influence the tablet properties such as acid resistance, disintegration property, dissolution property of active ingredient and the like, is not considered here.

While the detail is to be mentioned below in the Examples, since the tablet of the present invention contains talc at a predetermined ratio, and preferably an appropriate amount of a plasticizer, good polymer dispersibility can be obtained without using an alkali component. Moreover, since the tablet is further superior in acid resistance, it is superior as an enteric tablet. The tablet of the present invention free of an alkali component suppresses dissolution of an active ingredient from the tablet near the neutral range (around pH 4.5), as a result of which, a superior effect as an enteric tablet can be obtained in that the active ingredient dissolves for the first time after reaching the intestine.

The "active ingredient" in the present specification means a compound having a pharmacological action.

The "active ingredient" in the present specification is 4-[2-(4-methylphenylsulfanyl)phenyl]piperidine or a salt thereof, which is described in WO2003/029232.

4-[2-(4-Methylphenylsulfanyl)phenyl]piperidine and a salt thereof can be produced by the method described in the Examples of WO2003/029232.

As a salt of 4-[2-(4-methylphenylsulfanyl)phenyl]piperidine, a pharmacologically acceptable acid addition salt is preferable. As such salt, a salt with an inorganic acid (e.g., hydrochloric acid, hydrobromic acid, nitric acid, sulfuric acid, phosphoric acid etc.), or a salt with an organic acid (e.g., formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid etc.) and the like can be used. Among these, an inorganic acid salt is preferable, and hydrobromide is particularly preferable.

4-[2-(2-Methylphenylsulfanyl)phenyl]piperidine can be isolated and purified by a separation method known per se, for example, recrystallization, distillation, chromatography and the like.

When 4-[2-(4-methylphenylsulfanyl)phenyl]piperidine is obtained in a free form, it can be converted to an objective salt according to a method known per se or a method analogous thereto. On the contrary, when it is obtained as a salt, it can be converted to a free form or other objective salt according to a method known per se or a method analogous thereto.

4-[2-(4-Methylphenylsulfanyl)phenyl]piperidine may be a hydrate or a non-hydrate. Examples of the hydrate include monohydrate, 1.5 hydrate, 2 hydrate and the like. Furthermore, 4-[2-(4-methylphenylsulfanyl)phenyl]piperidine can also be present as a solvate with ethanol and the like.

The production method of the enteric tablet of the present invention is described in the following.

(1) Core Containing Active Ingredient

The core tablet to be applied with a coating with an enteric coating substrate in the present invention can be obtained by granulating and sieving using an active ingredient, an excipient and a binder, mixing the obtained sieved powder with a disintegrant and a lubricant and punching the mixture. As these excipient, binder, disintegrant and lubricant, those conventionally used for production of tablets can be used. In addition, each step of granulation, sieving, mixing, and tableting can be performed by conventionally-used methods.

While the excipient is not particularly limited, for example, one or more components selected from saccharides such as lactose, sucrose, mannitol and the like, starch, partly pregelatinized starch, cornstarch, microcrystalline cellulose, calcium phosphate, calcium sulfate, precipitated calcium carbonate, hydrated silicon dioxide and the like can be mentioned.

While the binder is not particularly limited, one or more kinds of components selected from oligosaccharides or sugar alcohols such as sucrose, glucose, lactose, maltose, sorbitol, mannitol and the like, polysaccharides such as dextrin, starch, sodium alginate, carageenan, guar gum, gum arabic, agar and the like, natural polymers such as tragacanth, gelatin, gluten and the like, cellulose derivatives such as methylcellulose, ethylcellulose, sodium carboxymethylcellulose, hydroxypropylcellulose, hydroxypropylmethylcellulose and the like, synthetic polymers such as polyvinylpyrrolidone, polyvinyl alcohol, polyvinyl acetate, polyethylene glycol, polyacrylic acid, polymethacrylic acid etc. and the like can be mentioned.

While the disintegrant is not particularly limited, one or more kinds of components selected from calcium carboxymethylcellulose, sodium starch glycolate, cornstarch, hydroxypropylstarch, partly pregelatinized starch, low-substituted hydroxypropylcellulose, croscarmellose calcium, croscarmellose sodium, crospovidone and the like can be mentioned.

While the lubricant is not particularly limited, those similar to those used for the above-mentioned enteric coating layer can be mentioned. Examples thereof include one or more kinds of components selected from talc, magnesium stearate, calcium stearate, colloidal silica, stearic acid, hydrated silicon dioxide, waxes, hydrogenated oil, polyethylene glycol, sodium benzoate, sodium stearyl fumarate and the like.

The size of the core tablet is preferably set to generally diameter 3-15 mm, preferably 5-8 mm.

(2) Tablet with Active Ingredient-Containing Core Coated with Enteric Coating Substrate The enteric coating substrate to be used for coating is as mentioned above. An enteric coating substrate can be used by dissolving an enteric polymer and talc in an organic solvent or in the form of aqueous latex or water dispersion. Where necessary, a plasticizer may also be used. Furthermore, a dry coating comprising directly spraying a mixed powder of a polymer and talc and simultaneously spraying a plasticizer may be performed.

The amount of the enteric coating substrate to be applied is set to about 4-8 mg/cm$^2$, preferably about 4-6 mg/cm$^2$, as the amount of the enteric polymer to be applied, based on the surface area of the core tablet.

The coating apparatus may be a conventionally-known means. For example, for spray coating, a pan coating apparatus, a drum coating apparatus, a fluidized bed coating apparatus, or a stirring fluidized bed coating apparatus may be used. As a spray device to be attached to such apparatuses, any of an air spray, an airless spray, a 3 fluid spray and the like can be used. For dry type, for example, centrifugal fluidized coating apparatus, pan coating apparatus, fluidized bed coating apparatus, centrifugal-rotary fluidized bed coating apparatus and the like can be mentioned.

The aforementioned enteric coating substrate and a coating apparatus are combined to perform enteric coating of an active ingredient-containing core tablet. After completion of the coating operation, drying by a conventional method, heat treatment, polish operation, sugar coating, coating using other coating base and the like may be performed.

Where necessary, an intermediate coating layer may be provided to block direct contact between the active ingredient and an enteric polymer. Such an intermediate coating layer may consist of plural layers.

Examples of the coating substance for an intermediate coating layer include polymer substrates such as low-substituted hydroxypropylcellulose, hydroxypropylcellulose, hydroxypropylmethylcellulose (hypromellose, e.g., TC-5 etc.), polyvinylpyrrolidone, polyvinyl alcohol, methylcellulose, hydroxyethylmethylcellulose and the like blended with sucrose [purified sucrose (pulverized (powder sugar) or not pulverized) etc.], starch sugars such as cornstarch and the like, saccharides such as lactose, honey and sugar alcohol (D-mannitol, erythritol etc.) and the like as appropriate, and the like. An intermediate coating layer may additionally contain, as appropriate, an excipient (e.g., light blocking agent (titanium dioxide etc.), an antistatic (titanium dioxide, talc etc.) and a binder (polyethylene glycol etc.) etc.), which are added as necessary for tableting mentioned below.

The amount of the intermediate coating layer to be applied is generally about 0.02 part by weight—about 0.10 part by weight, preferably about 0.02 part by weight—about 0.05 parts by weight, per 1 part by weight of the active ingredient-containing core tablet. The coating can be performed by a conventional method. For example, it is preferable to dilute these components of the intermediate coating layer with purified water etc. (intermediate layer coating solution) and spray the solution as a liquid. In this case, a binder such as hydroxypropylcellulose and the like is preferably sprayed therewith. Then, the intermediate coating layer can be coated with the enteric coating substrate.

The thus-produced enteric tablets can be evaluated for the enteric performance thereof by, for example, the presence or absence of dissolution of an active ingredient in the 1st fluid in the disintegrating test defined in the Japanese Pharmacopoeia or a buffer at around pH 4.5, evaluation of the amount of such acidic test solution penetrated into the tablet, and measurement of the disintegration time of the tablet in a neutral buffer represented by the 2nd fluid in the disintegrating test defined in the Japanese Pharmacopoeia.

The content of the active ingredient in the enteric tablet of the present invention is about 1-30 mg, preferably 5-20 mg, per tablet.

The present invention is explained in more detail in the following by referring to Examples, Comparative Example and Experimental Example, which are not to be construed as limitative. Various additives used in the Reference Examples, Examples, Comparative Example and Experimental Example were compatible products of the Japanese Pharmacopoeia, 15th Edition or Japanese Pharmaceutical Excipients 2003.

4-[2-(4-Methylphenylsulfanyl)phenyl]piperidine hydrobromide used in the Examples, Comparative Examples and Experimental Examples was appropriately produced according to the method described in the Examples of WO2003/029232 and the like. In addition, as methacrylic acid copolymer (dispersion), Eudragit (registered trade mark, L30D-55, manufactured by Evonic Industries AG) was used. Eudragit L30D-55 is a dispersion of a copolymer of methacrylic acid and ethyl acrylate (solid content concentration 30%), and contains polysorbate 80 and sodium lauryl sulfate. The composition ratio of the solid contents is methacrylic acid copolymer (97 wt %):polysorbate 80 (2.3 wt %):sodium lauryl sulfate (0.7 wt %).

EXAMPLES

Preparation of Enteric Coating Substrate 1 (Enteric Film Coating Solution 1: Talc 25 wt %)

The composition is shown in Table 1. Enteric coating substrate 1 (671.8 g, solid content concentration: 15 wt %) was prepared.

For preparation, titanium dioxide, red ferric oxide and yellow ferric oxide, which are poorly dispersible, were subjected to a disperser capable of applying a strong shear (rotation speed of about 10000 rpm), and the rest of the components was subjected to a stirrer (about 300-500 rpm) for separate preparation. Finally, they were mixed to give a coating solution (same in the following Examples). During coating, the coating solution was sprayed with stirring in a stirrer (about 300-500 rpm) to avoid coagulation and sedimentation of the solid components.

TABLE 1

| <Composition of enteric coating substrate 1> | |
|---|---|
| methacrylic acid copolymer (dispersion) | 18.67 mg |
| | (solid component 5.601 mg) |
| talc | 1.4 mg |

TABLE 1-continued

| <Composition of enteric coating substrate 1> | |
|---|---|
| triethyl citrate | 0.56 mg |
| titanium dioxide | 0.7 mg |
| red ferric oxide | 0.07 mg |
| yellow ferric oxide | 0.07 mg |
| purified water | 34.5 mg |
| Total (solid content) | 55.97 (8.401) mg |

Talc sediment was not confirmed in the obtained enteric coating substrate 1, and good dispersion was visually confirmed.

Preparation of Enteric Coating Substrate 2 (Enteric Film Coating Solution 2: Talc 25 wt %)

The composition is shown in Table 2. Enteric coating substrate 2 (3000.0 g, solid content concentration: 15 wt %) was prepared. For preparation, titanium dioxide, red ferric oxide and yellow ferric oxide, which are poorly dispersible, were subjected to a disperser capable of applying a strong shear (rotation speed of about 10000 rpm), and the rest of the components was subjected to a stirrer (about 300-500 rpm) for separate preparation. Finally, they were mixed to give a coating solution (same in the following Examples). During coating, the coating solution was sprayed with stirring in a stirrer (about 300-500 rpm) to avoid coagulation and sedimentation of the solid components.

TABLE 2

| <Composition of enteric coating substrate 2> | |
|---|---|
| methacrylic acid copolymer (dispersion) | 20.0 mg |
| | (solid component 6.0 mg) |
| talc | 1.5 mg |
| triethyl citrate | 0.6 mg |
| titanium dioxide | 0.75 mg |
| red ferric oxide | 0.075 mg |
| yellow ferric oxide | 0.075 mg |
| purified water | 37.0 mg |
| Total (solid content) | 60.0 (9.0) mg |

Talc sediment was not confirmed in the obtained enteric coating substrate 2, and good dispersion was visually confirmed.

Preparation of Enteric Coating Substrate 3 (Enteric Film Coating Solution 3: Talc 40 wt %)

The composition is shown in Table 3. Enteric coating substrate 3 (988.5 g, solid content concentration: 15 wt %) was prepared. For preparation, titanium dioxide, red ferric oxide and yellow ferric oxide, which are poorly dispersible, were subjected to a disperser capable of applying a strong shear (rotation speed of about 10000 rpm), and the rest of the components was subjected to a stirrer (about 300-500 rpm) for separate preparation. Finally, they were mixed to give a coating solution (same in the following Examples). During coating, the coating solution was sprayed with stirring in a stirrer (about 300-500 rpm) to avoid coagulation and sedimentation of the solid components.

TABLE 3

| <Composition of enteric coating substrate 3> | |
|---|---|
| methacrylic acid copolymer (dispersion) | 20.00 mg |
| | (solid component 6.0 mg) |
| talc | 2.4 mg |
| triethyl citrate | 0.6 mg |

TABLE 3-continued

<Composition of enteric coating substrate 3>

| | |
|---|---|
| titanium dioxide | 0.75 mg |
| red ferric oxide | 0.075 mg |
| yellow ferric oxide | 0.075 mg |
| purified water | 42 mg |
| Total (solid content) | 65.9 (9.9) mg |

Talc sediment was not confirmed in the obtained enteric coating substrate 3, and practicality of the dispersibility was visually confirmed.

Preparation of Intermediate Layer Coating Solution

The composition is shown in Table 4. An intermediate layer coating solution (562.5 g, solid content concentration: 10% by weight) was prepared.

TABLE 4

| | |
|---|---|
| hypromellose | 2.8125 mg |
| macrogol 6000 | 0.5625 mg |
| talc | 0.375 mg |
| purified water | 33.750 mg |
| Total (solid content) | 37.50 (3.75) mg |

Production of core tablet of 4-[2-(4-methylphenylsulfanyl)phenyl]piperidine hydrobromide (hereinafter abbreviated as "compound A")

(Production of 5 mg Core Tablet)

A core tablet containing compound A was produced as follows at a composition ratio shown in Table 5.

To be specific, compound A (3148 g, content amended), mannitol (54180 g, weight amended) and microcrystalline cellulose (7350 g) were placed in a fluid bed granulation dryer (FD-WSG-60, manufactured by POWREX), preheated and mixed. An aqueous solution (36781 g) of hydroxypropylcellulose (2505 g, charge increased) in water (39.25 L) was sprayed to give a granulated powder. The obtained granulated powder (64440 g) was sieved through Power Mill (P-7S, manufactured by SHOWA KAGAKU KIKAI CO., LTD.) to give a sieved powder. The sieved powder (62800 g), microcrystalline cellulose (3450 g), sodium starch glycolate (2070 g) and magnesium stearate (690.0 g) were placed in a tumbler mixer (TM-400S, manufactured by SHOWA KAGAKU KIKAI CO., LTD.) and mixed to give a mixed powder. The mixed powder was tableted in a rotary tableting machine (AQUA0836SS2JII, manufactured by KIKUSUI SEISAKUSHO LTD.) with a punch (150 mg per tablet, 7 mmφ) to give a core tablet.

TABLE 5

<Composition of 5 mg core tablet containing compound A>

| | |
|---|---|
| compound A | 6.425 mg |
| mannitol | 110.575 mg |
| microcrystalline cellulose | 22.5 mg |
| hydroxypropylcellulose | 4.5 mg |
| sodium starch glycolate | 4.5 mg |
| magnesium stearate | 1.5 mg |
| Total | 150 mg |

(Production of 10 mg Core Tablet)

A core tablet containing compound A was produced as follows at a composition ratio shown in Table 6.

To be specific, compound A (473.6 g, content amended), mannitol (3855 g, weight amended) and microcrystalline cellulose (555.0 g) were placed in a fluid bed granulation dryer (FD-5S, manufactured by POWREX), and preheated and mixed. An aqueous solution (2776 g) of hydroxypropylcellulose (166.5 g) was sprayed to give a granulated powder. The obtained granulated powder (4573 g) was sieved through Power Mill (P-3, manufactured by SHOWA KAGAKU KIKAI CO., LTD.) to give a sieved powder. The sieved powder (4095 g), microcrystalline cellulose (225.0 g), sodium starch glycolate (135.0 g) and magnesium stearate (45.00 g) were placed in a tumbler mixer (TM-15S, manufactured by SHOWA KAGAKU KIKAI CO., LTD.) and mixed to give a mixed powder. The mixed powder was tableted in a rotary tableting machine (AQUA08242L2J1, manufactured by KIKUSUI SEISAKUSHO LTD.) with a punch (150 mg per tablet, 7 mmφ) to give a core tablet.

TABLE 6

<Composition of 10 mg core tablet containing compound A>

| | |
|---|---|
| compound A | 12.85 mg |
| mannitol | 104.15 mg |
| microcrystalline cellulose | 22.5 mg |
| hydroxypropylcellulose | 4.5 mg |
| sodium starch glycolate | 4.5 mg |
| magnesium stearate | 1.5 mg |
| Total | 150 mg |

(Production of 20 mg Core Tablet)

A core tablet containing compound A was produced as follows at a composition ratio shown in Table 7.

To be specific, compound A (12590 g, content amended), mannitol (44740 g, weight amended) and microcrystalline cellulose (7350 g) were placed in a fluid bed granulation dryer (FD-WSG-60, manufactured by POWREX), and preheated and mixed. An aqueous solution (36799 g) of hydroxypropylcellulose (2505 g, charge increased) in water (39.25 L) was sprayed to give a granulated powder. The obtained granulated powder (64440 g) was sieved through Power Mill (P-7S, manufactured by SHOWA KAGAKU KIKAI CO., LTD.) to give a sieved powder. The sieved powder (62800 g), microcrystalline cellulose (3450 g), sodium starch glycolate (2070 g) and magnesium stearate (690.0 g) were placed in a tumbler mixer (TM-400S, manufactured by SHOWA KAGAKU KIKAI CO., LTD.) and mixed to give a mixed powder. The mixed powder was tableted in a rotary tableting machine (AQUA0836SS2JII, manufactured by KIKUSUI SEISAKUSHO LTD.) with a punch (150 mg per tablet, 7 mmφ) to give a core tablet.

TABLE 7

<Composition of 20 mg core tablet containing compound A>

| | |
|---|---|
| compound A | 25.7 mg |
| mannitol | 91.3 mg |
| microcrystalline cellulose | 22.5 mg |
| hydroxypropylcellulose | 4.5 mg |
| sodium starch glycolate | 4.5 mg |
| magnesium stearate | 1.5 mg |
| Total | 150 mg |

Example 1

Production of Enteric Tablet (5 mg Tablet) of Compound A

A 5 mg core tablet (58200 g) containing compound A was placed in a film coating machine (DRC-1200DS, manufactured by POWREX), and enteric coating substrate 2 (29933 g) was sprayed to give an enteric tablet (about 159.5 mg per tablet, about 4.8 mg/cm$^2$ coating).

Example 2

Production of Enteric Tablet (10 mg Tablet) of Compound A

A 10 mg core tablet (3300 g) containing compound A was placed in a film coating machine (DRC-500, manufactured by POWREX), and enteric coating substrate 2 (1400.0 g) was sprayed to give an enteric tablet (about 158.4 mg per tablet, about 4.8 mg/cm$^2$ coating).

Example 3

Production of Enteric Tablet (20 mg Tablet) of Compound A

A 20 mg core tablet (58200 g) containing compound A was placed in a film coating machine (DRC-1200DS, manufactured by POWREX), and enteric coating substrate 2 (23493 g) was sprayed to give an enteric tablet (about 159.2 mg per tablet, about 4.8 mg/cm$^2$ coating).

Example 4

Production of Enteric Tablet (5 mg Tablet) of Compound A

A 5 mg core tablet (58200 g) containing compound A was placed in a film coating machine (DRC-1200DS, manufactured by POWREX), and enteric coating substrate 2 (14653 g) was sprayed to give an enteric tablet (about 155.0 mg per tablet, about 2.4 mg/cm$^2$ coating).

Example 5

Production of Enteric Tablet (5 mg Tablet) of Compound A

A 5 mg core tablet (58200 g) containing compound A was placed in a film coating machine (DRC-1200DS, manufactured by POWREX), and enteric coating substrate 2 (20044 g) was sprayed to give an enteric tablet (about 156.6 mg per tablet, about 3.2 mg/cm$^2$ coating).

Example 6

Production of Enteric Tablet (5 mg Tablet) of is Compound A

A 5 mg core tablet (58200 g) containing compound A was placed in a film coating machine (DRC-1200DS, manufactured by POWREX), and enteric coating substrate 2 (24721 g) was sprayed to give an enteric tablet (about 157.9 mg per tablet, about 4.0 mg/cm$^2$ coating).

Example 7

Production of Enteric Tablet (5 mg Tablet) of Compound A

A 5 mg core tablet (58200 g) containing compound A' was placed in a film coating machine (DRC-1200DS, manufactured by POWREX), and enteric coating substrate 2 (33101 g) was sprayed to give an enteric tablet (about 160.5 mg per tablet, about 5.6 mg/cm$^2$ coating).

Example 8

Production of Enteric Tablet (5 mg Tablet) of Compound A

A 5 mg core tablet (58200 g) containing compound A was placed in a film coating machine (DRC-1200DS, manufactured by POWREX), and enteric coating substrate 2 (39034 g) was sprayed to give an enteric tablet (about 162.4 mg per tablet, about 6.4 mg/cm$^2$ coating).

Example 9

Production of Enteric Tablet (20 mg Tablet) of Compound A

A 20 mg core tablet (58200 g) containing compound A was placed in a film coating machine (DRC-1200DS, manufactured by POWREX), and enteric coating substrate 2 (14540 g) was sprayed to give an enteric tablet (about 154.4 mg per tablet, about 2.4 mg/cm$^2$ coating).

Example 10

Production of Enteric Tablet (20 mg Tablet) of Compound A

A 20 mg core tablet (58200 g) containing compound A was placed in a film coating machine (DRC-1200DS, manufactured by POWREX), and enteric coating substrate 2 (18891 g) was sprayed to give an enteric tablet (about 155.9 mg per tablet, about 3.2 mg/cm$^2$ coating).

Example 11

Production of Enteric Tablet (20 mg Tablet) of Compound A

A 20 mg core tablet (58200 g) containing compound A was placed in a film coating machine (DRC-1200DS, manufactured by POWREX), and enteric coating substrate 2 (22126 g) was sprayed to give an enteric tablet (about 157.3 mg per tablet, about 4.0 mg/cm$^2$ coating).

Example 12

Production of Enteric Tablet (20 mg Tablet) of Compound A

A 20 mg core tablet (58200 g) containing compound A was placed in a film coating machine (DRC-1200DS, manufactured by POWREX), and enteric coating substrate 2 (28977 g) was sprayed to give an enteric tablet (about 160.3 mg per tablet, about 5.6 mg/cm$^2$ coating).

Example 13

Production of Enteric Tablet (20 mg Tablet) of Compound A

A 20 mg core tablet (58200 g) containing compound A was placed in a film coating machine (DRC-1200DS, manufactured by POWREX), and enteric coating substrate 2 (37010 g) was sprayed to give an enteric tablet (about 162.0 mg per tablet, about 6.4 mg/cm$^2$ coating).

Example 14

Production of Enteric Tablet (5 mg Tablet) of Compound A

A 5 mg core tablet (80.0 g) containing compound A was placed in a film coating machine (HC-LABO30, manufactured by Freund Corporation), and an intermediate layer coating solution (63.3 g) was sprayed to give an intermediate layer coated tablet (about 154.1 mg per tablet).

Then, the obtained intermediate layer coated tablet (42.0 g) was placed in a film coating machine (HC-LABO30, manufactured by Freund Corporation), and enteric coating substrate 2 (91.5 g) was sprayed to give an enteric tablet (about 162.6 mg per tablet, about 4.8 mg/cm$^2$ coating).

Example 15

Production of Enteric Tablet (20 mg Tablet) of Compound A

A 20 mg core tablet (86.0 g) containing compound A was placed in a film coating machine (HC-LABO30, manufactured by Freund Corporation), and an intermediate layer coating solution (60.0 g) was sprayed to give an intermediate layer coated tablet (about 153.5 mg per tablet).

Then, the obtained intermediate layer coated tablet (43.0 g) was placed in a film coating machine (HC-LABO30, manufactured by Freund Corporation), and enteric coating substrate 2 (82.6 g) was sprayed to give an enteric tablet (about 162.6 mg per tablet, about 4.8 mg/cm$^2$ coating).

Experimental Example 1

Acid Resistance Test of Enteric Tablet (1) (Influence of Principal Agent Content)

The acid resistance and disintegration property of the enteric tablets obtained in Examples 1-3 were examined by the disintegration test method of the Japanese Pharmacopoeia, 15th Edition. Using an acid resistance test solution (0.1N hydrochloric acid or pH 4.5 acetic acid buffer), the test was performed for 120 min, and Acid Uptake was measured from the changes in the tablet weight before and after the test. Then, the tablet was transferred to a disintegration test solution (pH 6.8 phosphoric acid buffer), and the disintegration time in the test solution was measured. The Acid Uptake is an evaluation method of the acid resistance of enteric film. When the value is not more than 10%, the tablet is free of water penetration into the inside. Thus, it is one index to judge the presence of sufficient acid resistance of the enteric film. The Acid Uptake was calculated from the following formula.

$$\text{Acid Uptake}(\%) = (\text{tablet weight after test} - \text{tablet weight before test})/\text{tablet weight before test} \times 100$$

The Acid Uptake and the disintegration time of the enteric tablets obtained in Examples 1-3 are shown in Tables 8 and 9.

TABLE 8

Results in acid resistance test solution (0.1N hydrochloric acid) and disintegration test solution (pH 6.8 phosphoric acid buffer) (n = 6)

|  | Ex. 1 | Ex. 2 | Ex. 3 |
|---|---|---|---|
| Acid Uptake (%) | 4.5 | 4.6 | 4.5 |
| disintegration time (min) | 6.6 | 7.7 | 7.8 |

TABLE 9

Results in acid resistance test solution (pH 4.5 acetic acid buffer) and disintegration test solution (pH 6.8 phosphoric acid buffer) (n = 6)

|  | Ex. 1 | Ex. 2 | Ex. 3 |
|---|---|---|---|
| Acid Uptake (%) | 6.2 | 5.7 | 6.0 |
| disintegration time (min) | 7.2 | 8.9 | 11.6 |

Experimental Example 2

Acid Resistance Test of Enteric Tablet (2) (5 mg Tablet, Influence of Coating Amount)

The acid resistance and disintegration property of the enteric tablets obtained in Examples 1, 4-8 were examined by the disintegration test method of the Japanese Pharmacopoeia, 15th Edition. Using an acid resistance test solution (0.1N hydrochloric acid or pH 4.5 acetic acid buffer), the test was performed for 120 min, and Acid Uptake was measured from the changes in the tablet weight before and after the test. Then, the tablet was transferred to a disintegration test solution (pH 6.8 phosphoric acid buffer), and the disintegration time in the test solution was measured. The Acid Uptake and the disintegration time of the enteric tablets obtained in Examples 1, 4-8 are shown in Tables 10 and 11.

TABLE 10

Results in acid resistance test solution (0.1N hydrochloric acid) and disintegration test solution (pH 6.8 phosphoric acid buffer) (n = 6)

|  | Ex. 4 | Ex. 5 | Ex. 6 | Ex. 1 | Ex. 7 | Ex. 8 |
|---|---|---|---|---|---|---|
| Acid Uptake (%) | 21.5 | 17.5 | 8.8 | 4.5 | 4.8 | 4.3 |
| disintegration time (min) | 6.5 | 6.6 | 7.0 | 6.6 | 8.8 | 8.6 |

TABLE 11

Results in acid resistance test solution (pH 4.5 acetic acid buffer) and disintegration test solution (pH 6.8 phosphoric acid buffer) (n = 6)

|  | Ex. 4 | Ex. 5 | Ex. 6 | Ex. 1 | Ex. 7 | Ex. 8 |
|---|---|---|---|---|---|---|
| Acid Uptake (%) | 51.5 | 37.2 | 8.5 | 6.2 | 6.0 | 5.1 |
| disintegration time (min) | 13.6 | 10.9 | 7.1 | 7.2 | 9.0 | 9.5 |

Experimental Example 3

Acid Resistance Test of Enteric Tablet (3) (20 mg Tablet, Influence of Coating Amount)

The acid resistance and disintegration property of the enteric tablets obtained in Examples 3, 9-13 were examined by the disintegration test method of the Japanese Pharmacopoeia. Using an acid resistance test solution (0.1N hydrochloric acid or pH 4.5 acetic acid buffer), the test was performed for 120 min, and Acid Uptake was measured from the changes in the tablet weight before and after the test. Then, the tablet was transferred to a disintegration test solution (pH 6.8 phosphoric acid buffer), and the disintegration time to in the test solution was measured. The Acid Uptake and the disintegration time of the enteric tablets obtained in Examples 3, 9-13 are shown in Tables 12 and 13.

TABLE 12

Results in acid resistance test solution (0.1N hydrochloric acid) and disintegration test solution (pH 6.8 phosphoric acid buffer) (n = 6)

|  | Ex. 9 | Ex. 10 | Ex. 11 | Ex. 3 | Ex. 12 | Ex. 13 |
|---|---|---|---|---|---|---|
| Acid Uptake (%) | 21.8 | 6.6 | 5.9 | 4.5 | 4.5 | 4.2 |
| disintegration time (min) | 9.4 | 11.4 | 7.6 | 7.8 | 8.5 | 10.0 |

TABLE 13

Results in acid resistance test solution (pH 4.5, acetic acid buffer) and disintegration test solution (pH 6.8 phosphoric acid buffer) (n = 6)

|  | Ex. 9 | Ex. 10 | Ex. 11 | Ex. 3 | Ex. 12 | Ex. 13 |
|---|---|---|---|---|---|---|
| Acid Uptake (%) | 43.3 | 29.0 | 7.9 | 6.0 | 5.5 | 5.2 |
| disintegration time (min) | 23.7 | 22.9 | 9.9 | 11.6 | 11.9 | 12.0 |

From these results, it is shown that the enteric tablet of the present invention, which is free of an alkali component in the enteric coating layer, has superior acid resistance or disintegration property.

Comparative Example

Preparation of Enteric Coating Substrate 4 (Enteric Film Coating Solution 3: Talc 50 wt %)

The composition is shown in Table 14. An enteric coating substrate 4 (641.0 g, solid content concentration: 25 wt %) was prepared.

TABLE 14

<Composition of enteric coating substrate 4>

| methacrylic acid copolymer (dispersion) | 18.67 mg (solid component 5.601 mg) |
|---|---|
| talc | 2.8 mg |
| triethyl citrate | 0.56 mg |
| titanium dioxide | 0.9 mg |
| red ferric oxide | 0.07 mg |
| yellow ferric oxide | 0.07 mg |
| purified water | 17 mg |
| Total (solid content) | 40.07 (10.001) mg |

It was visually confirmed that the obtained enteric coating substrate 4 was insufficient in talc dispersion, and sediment was remarkable.

In the enteric coating substrates 1 and 2 with the talc amount (amount of talc relative to polymer components) of 25 wt %, sediment of talc was not confirmed but good dispersion was visually confirmed. In addition, in the enteric coating substrate 3 with 40 wt %, practical dispersibility was confirmed. Therefore, it was confirmed that a decreased talc amount affords good talc dispersibility and enhanced producibility.

The core tablet part itself of the enteric tablets represented by the above-mentioned Examples is useful as a "rapidly disintegrating tablet". The "rapidly disintegrating tablet" may be film-coated. Specific formulations are explained in the following by way of Reference Examples.

Reference Example 1

Production of Rapidly Disintegrating Tablet (5 mg Tablet) of Compound A

A core tablet containing compound A was produced as follows at a composition ratio shown in Table 15.

To be specific, compound A (3148 g, content amended), mannitol (54180 g, weight amended) and microcrystalline cellulose (7350 g) were placed in a fluid bed granulation dryer (FD-WSG-60, manufactured by POWREX), preheated and mixed. An aqueous solution (36801 g) of hydroxypropylcellulose (2505 g, charged in increased amount) in water (39.25 L) was sprayed to give a granulated powder. The obtained granulated powder (64440 g) was sieved through Power Mill (P-7S, manufactured by SHOWA KAGAKU KIKAI CO., LTD.) to give a sieved powder. The sieved powder (62800 g), microcrystalline cellulose (3450 g), sodium starch glycolate (2070 g) and magnesium stearate (690 g) were placed in a tumbler mixer (TM-400S, manufactured by SHOWA KAGAKU KIKAI CO., LTD.) and mixed to give a mixed powder. The mixed powder was tableted in a rotary tableting machine (AQUA0836SS2JII, manufactured by KIKUSUI SEISAKUSHO LTD.) with a punch (150 mg per tablet, 7 mmφ) to give a core tablet.

TABLE 15

<Composition of core tablet containing compound A>

| compound A | 6.425 mg |
|---|---|
| mannitol | 110.575 mg |
| microcrystalline cellulose | 22.5 mg |
| hydroxypropylcellulose | 4.5 mg |
| sodium starch glycolate | 4.5 mg |
| magnesium stearate | 1.5 mg |
| Total | 150 mg |

The obtained core tablets (58200 g) were placed in a film coating machine (DRC-1200DS, manufactured by POWREX), and a coating solution (27674 g) at a composition ratio shown in Table 16 was sprayed to give rapidly disintegrating tablets (about 156.1 mg per tablet).

TABLE 16

<Composition of coating solution>

| hypromellose | 4.5 mg |
|---|---|
| macrogol 6000 | 1 mg |
| titanium dioxide | 0.5 mg |

TABLE 16-continued

| <Composition of coating solution> | |
|---|---|
| red ferric oxide | 0.033 mg |
| yellow ferric oxide | 0.067 mg |
| purified water | 54.9 mg |
| total (solid content) | 61 (6.1) mg |

Reference Example 2

Production of Rapidly Disintegrating Tablet (10 mg Tablet) of Compound A

A core tablet containing compound A was produced as follows at a composition ratio shown in Table 17.

To be specific, compound A (6297 g, content amended), mannitol (51030 g, weight amended) and microcrystalline cellulose (7350 g) were placed in a fluid bed granulation dryer (FD-WSG-60, manufactured by POWREX), preheated and mixed. An aqueous solution (36797 g) of hydroxypropylcellulose (2505 g, charged in increased amount) in water (39.25 L) was sprayed to give a granulated powder. The obtained granulated powder (64440 g) was sieved through Power Mill (P-7S, manufactured by SHOWA KAGAKU KIKAI CO., LTD.) to give a sieved powder. The sieved powder (62800 g), microcrystalline cellulose (3450 g), sodium starch glycolate (2070 g) and magnesium stearate (690.0 g) were placed in a tumbler mixer (TM-400S, manufactured by SHOWA KAGAKU KIKAI CO., LTD.) and mixed to give a mixed powder. The mixed powder was tableted in a rotary tableting machine (AQUA0836SS2JII, manufactured by KIKUSUI SEISAKUSHO LTD.) with a punch (150 mg per tablet, 7 mmφ) to give a core tablet.

TABLE 17

| <Composition of core tablet containing compound A> | |
|---|---|
| compound A | 12.85 mg |
| mannitol | 104.15 mg |
| microcrystalline cellulose | 22.5 mg |
| hydroxypropylcellulose | 4.5 mg |
| sodium starch glycolate | 4.5 mg |
| magnesium stearate | 1.5 mg |
| Total | 150 mg |

The obtained core tablets (58200 g) were placed in a film coating machine (DRC-1200DS, manufactured by POWREX), and a coating solution (27803 g) at a composition ratio shown in Table 16 was sprayed to give rapidly disintegrating tablets (about 156.1 mg per tablet).

Reference Example 3

Production of Rapidly Disintegrating Tablet (20 mg Tablet) of Compound A

A core tablet containing compound A was produced as follows at a composition ratio shown in Table 18.

To be specific, compound A (12590 g, content amended), mannitol (44740 g, weight amended) and microcrystalline cellulose (7350 g) were placed in a fluid bed granulation dryer (FD-WSG-60, manufactured by POWREX), preheated and mixed. An aqueous solution (36800 g) of hydroxypropylcellulose (2505 g, charged in increased amount) in water (39.25 L) was sprayed to give a granulated powder. The obtained granulated powder (64440 g) was sieved through Power Mill (P-7S, manufactured by SHOWA KAGAKU KIKAI CO., LTD.) to give a sieved powder. The sieved powder (62800 g), microcrystalline cellulose (3450 g), sodium starch glycolate (2070 g) and magnesium stearate (690.0 g) were placed in a tumbler mixer (TM-400S, manufactured by SHOWA KAGAKU KIKAI CO., LTD.) and mixed to give a mixed powder. The mixed powder was tableted in a rotary tableting machine (AQUA0836SS2JII, manufactured by KIKUSUI SEISAKUSHO LTD.) with a punch (150 mg per tablet, 7 mmφ) to give a core tablet.

TABLE 18

| <Composition of core tablet containing compound A> | |
|---|---|
| compound A | 25.7 mg |
| mannitol | 91.3 mg |
| microcrystalline cellulose | 22.5 mg |
| hydroxypropylcellulose | 4.5 mg |
| sodium starch glycolate | 4.5 mg |
| magnesium stearate | 1.5 mg |
| Total | 150 mg |

The obtained core tablets (58200 g) were placed in a film coating machine (DRC-1200DS, manufactured by POWREX), and a coating solution (27336 g) at a composition ratio shown in Table 16 was sprayed to give rapidly disintegrating tablets (about 156.1 mg per tablet).

INDUSTRIAL APPLICABILITY

Using the enteric tablet of the present invention, infiltration of the gastric juice into a tablet can be prevented by improved acid resistance of the tablet, which in turn suppresses gelation of the tablet and permits rapid disintegration after reaching the intestine and dissolution of the active ingredient. As a result, the bioavailability of the active ingredient is improved.

While some of the embodiments of the present invention have been described in detail in the above, it is, however, possible for those of ordinary skill in the art to make various modifications and changes to the particular embodiments shown without substantially departing from the teaching and advantages of the present invention. Such modifications and changes are encompassed in the spirit and scope of the present invention as set forth in the appended claims.

This application is based on a patent application No. 2010-105668 filed in Japan, the contents of which are incorporated in full herein.

The invention claimed is:

1. An enteric tablet comprising:
   1) a core tablet comprising 4-[2-(4-methylphenylsulfanyl) phenyl]piperidine or a salt thereof, and
   2) an enteric coating layer comprising a) a polymer component comprising a methacrylic acid copolymer, and b) talc in a weight of 10 to 25% relative to the weight of said polymer component, and c) substantially no alkali component,
   wherein the weight of said polymer component to the surface area of the core tablet is 4 to 6 mg/cm$^2$.

2. The enteric tablet of claim 1, wherein the methacrylic acid copolymer is
   1) a copolymer of methacrylic acid and ethyl acrylate,
   2) a copolymer of methacrylic acid and methyl methacrylate, or
   3) a copolymer of methacrylic acid, methyl acrylate and methyl methacrylate.

3. The enteric tablet of claim 1, wherein the enteric coating layer further comprises a plasticizer.

* * * * *